US00PP33107P2

(12) United States Plant Patent
Asanoma

(10) Patent No.: US PP33,107 P2
(45) Date of Patent: May 25, 2021

(54) ***SEDUM* PLANT NAMED 'TAT1801'**

(50) Latin Name: *Sedum spurium*
Varietal Denomination: TAT1801

(71) Applicant: Asanoma Engei, Kitashitara-gun (JP)

(72) Inventor: Tatsuya Asanoma, Aichi-prefecture (JP)

(73) Assignee: Asanoma Engei

( * ) Notice: Subject to any disclaimer, the term of this patent is extended or adjusted under 35 U.S.C. 154(b) by 0 days.

(21) Appl. No.: 16/873,435

(22) Filed: Apr. 10, 2020

(51) Int. Cl.
*A01H 5/02* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 6/328; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Sedum spurium* plant named 'TAT1801' is disclosed, characterized light green foliage with a distinct creamy margin. Plants are low growing, having a groundcover habit. This is a low maintenance plant with drought and heat resistance. The new variety is a *Sedum*, plants are useful for a variety of ornamental purposes, including outdoor containers and landscape.

3 Drawing Sheets

Latin name of the genus and species: *Sedum spurium.*
Variety denomination: 'TAT1801'.

BACKGROUND OF THE INVENTION

The new *Sedum* cultivar is the product of chance discovery. The new variety was discovered as a naturally occurring branch mutation of the parent variety, *Sedum spurium* 'Tricolor', unpatented.

The discovery was made in the inventor's garden in Aichi-prefecture, Japan, during May of 2016.

Asexual reproduction of the new cultivar 'TAT1801' was first performed in Aichi-prefecture, Japan by terminal vegetative cuttings in the Summer of 2016. 'TAT1801' has since produced multiple generations and has shown that the unique features of this cultivar are stable and reproduced true to type.

SUMMARY OF THE INVENTION

The cultivar 'TAT1801' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TAT1801'. These characteristics in combination distinguish 'TAT1801' as a new and distinct *Sedum spruium* cultivar:

1. Light green foliage with a distinct creamy yellow margin.
2. Low growing, groundcover habit.
3. Drought resistant.
4. Heat resistant.
5. Low maintenance plant.

PARENTAL COMPARISON

Plants of the new cultivar 'TAT1801' are similar to plants of the parent, in most horticultural characteristics, however, plants of the new cultivar 'TAT1801' differ in the following;

1. Foliage of the new variety is light green with a creamy yellow margin, the parent variety is green and white variegated with pink margins.

COMMERCIAL COMPARISON

Plants of the new cultivar 'TAT1801' are comparable to *Sedum* 'Fool's Gold', unpatented. Plants are similar in most horticultural characteristics; however, the new variety 'TAT1801' differs in the following:

1. Foliage of the new variety is light green with a creamy yellow margin, foliage of this comparator is green and yellow variegated with pink margins.

BRIEF DESCRIPTION OF THE PHOTOGRAPHS

The accompanying photograph in FIG. 1 illustrates in full color a typical plants plant of 'TAT1801' grown outdoors in Boskoop, NL. Age of the plant is approximately 12 months.

Figure 1:
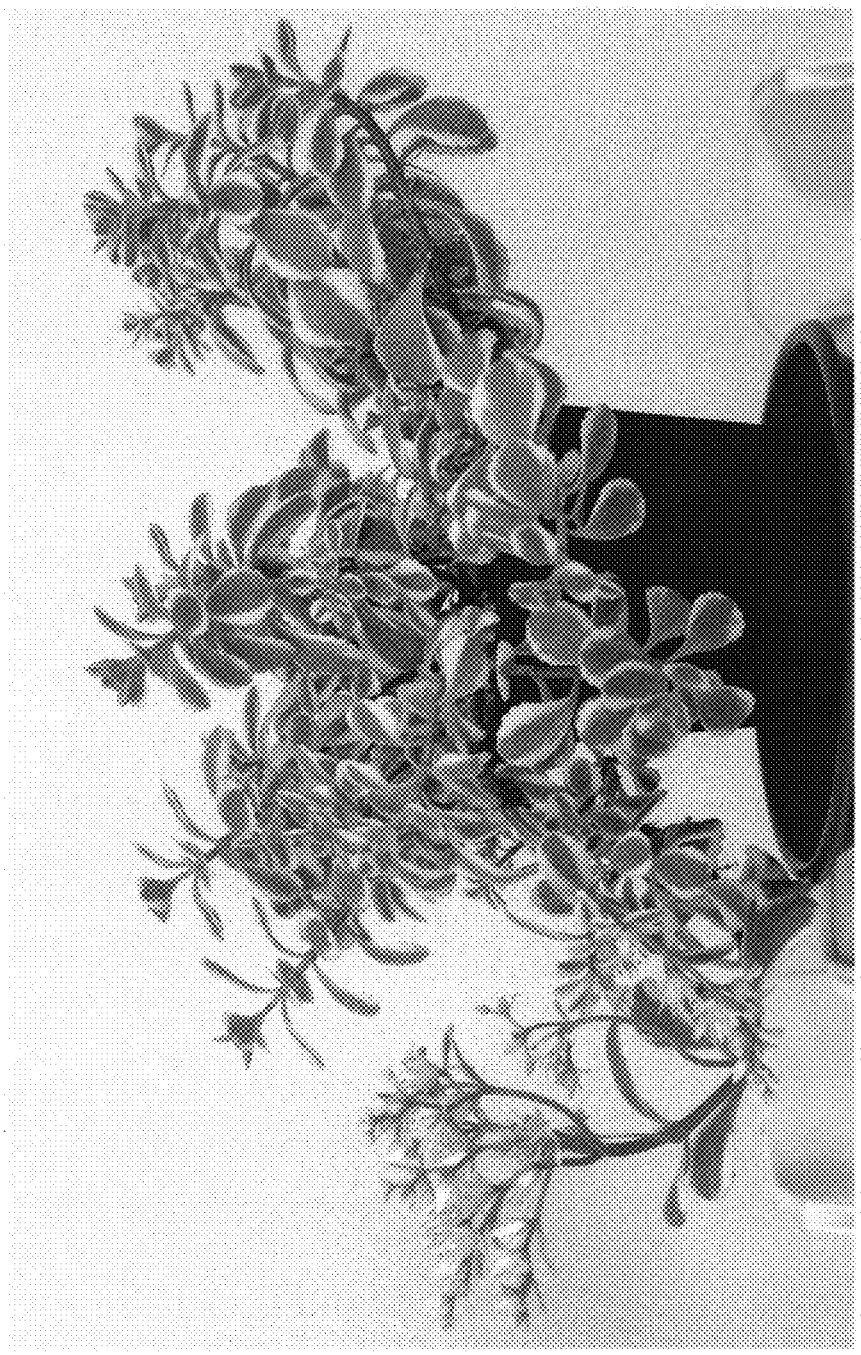
Figure 2:
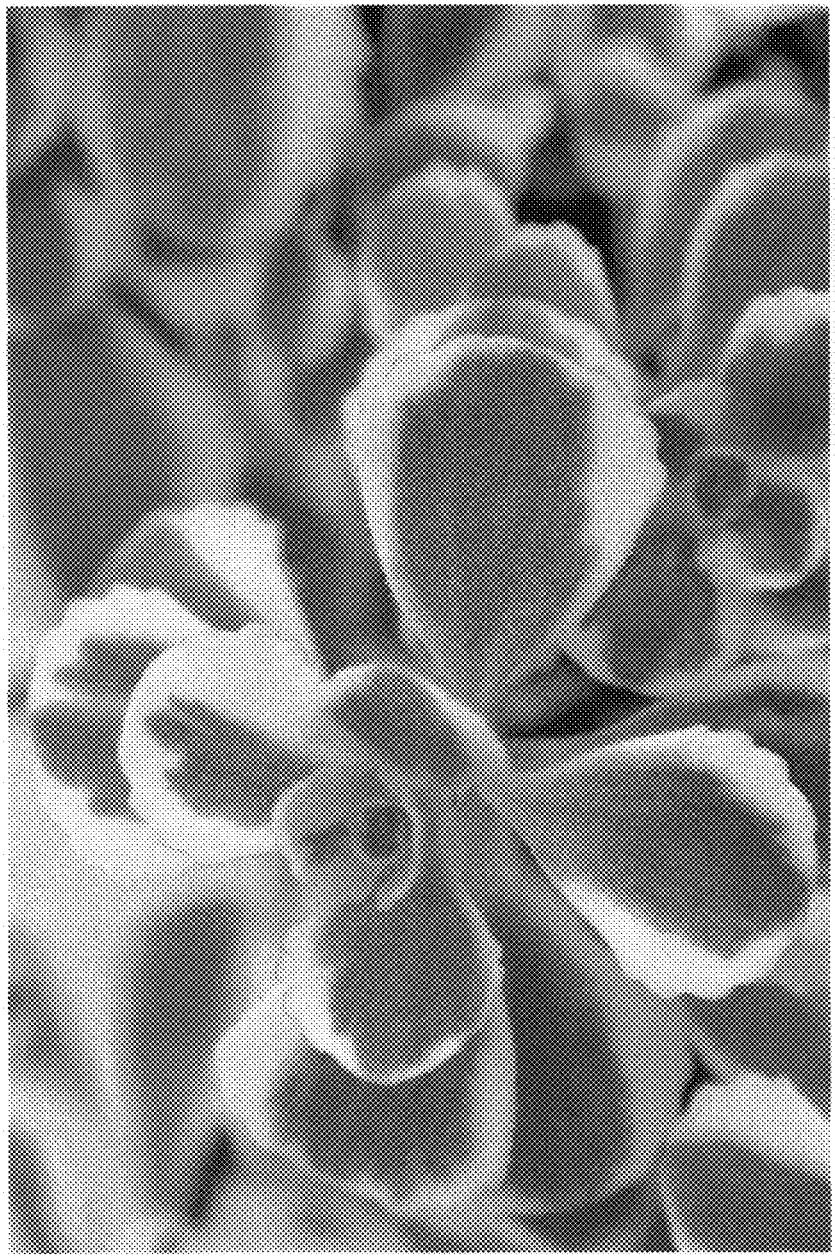
FIG. 2 illustrates a close-up view of the foliage.
Figure 3:
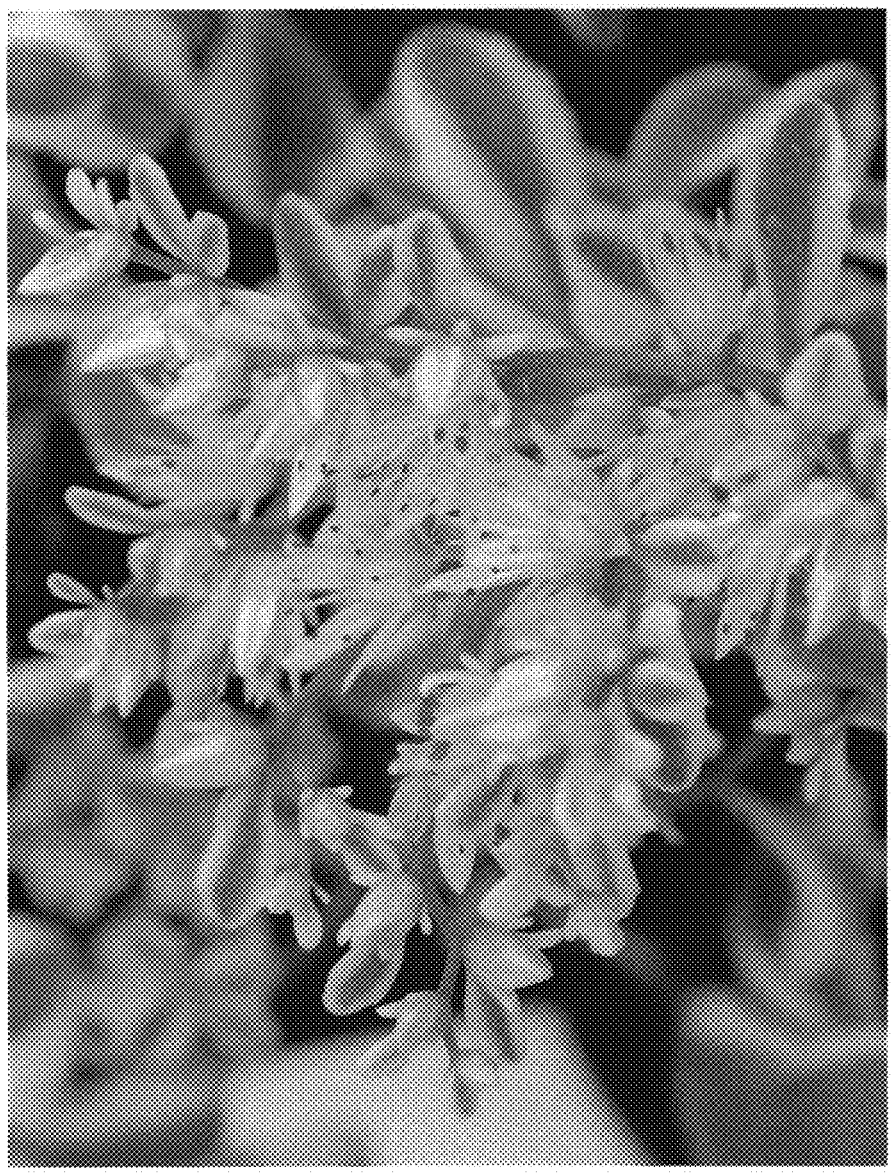
FIG. 3 illustrates a close-up view of the foliage and flowers.

The photographs were taken using conventional techniques and although colors may appear different from actual colors due to light reflectance it is as accurate as possible by conventional photographic techniques.

No artificial light, photoperiodic treatments or chemical treatments were given to the plants.

DETAILED BOTANICAL DESCRIPTION

In the following description, color references are made to The Royal Horticultural Society Colour Chart, 2015 except where general terms of ordinary dictionary significance are used. The following observations and measurements describe 'TAT1801' plants grown outdoors in Boskoop, NL. Temperatures ranged from approximately 18° C. to 30° C. during the day and approximately 8° C. to 20° C. at night.

No artificial light, photoperiodic treatments or chemical treatments were given to the plants. Measurements and numerical values represent averages of typical plant types. Botanical classification: *Sedum spurium* 'TAT1801'.

PROPAGATION

Type of propagation typically used: Terminal vegetative cuttings.

Time to initiate roots: About 14 days at approximately 22° C.

Root description: Fibrous, brown, not accurately measured with a color chart.

PLANT

Age of plant described: Approximately 12 months.

Container size of the plant described: 9 cm.

Growth habit: Herbaceous perennial, trailing habit.

Height: Approximately 14.9 cm to top of highest leaf. Approximately 9.7 cm to top of highest inflorescence.

Plant spread: 30.4 cm.

Growth rate: Moderate.

Branching characteristics: Free branching, lateral branches. Pinching is not required, but increases branching.

Length of primary lateral branches: Average 14.4 cm.

Diameter of lateral branches: 3 mm.

Quantity of primary lateral branches: About 21.

*Secondary branches*.—Average 60 per plant.

Characteristics of primary lateral branches:

*Form*.—Round.

*Color*.—Developing: Near RHS Yellow-Green 149B, lower section near N148B. Mature: Near RHS Greyed-Brown 199A and 199D, colors present individually. At Nodes: Near RHS Greyed-Brown 199A.

*Texture*.—Glabrous.

*Strength*.—Strong.

*Appearance*.—Slightly glossy.

*Aspect*.—Main stems in an average angle of 50° (varying between 20° and 90°).

Internode length: Average 1.2 cm.

FOLIAGE

Leaf:

*Arrangement*.—Opposite, single.

*Quantity*.—24 (12 pairs) per branch.

*Average length*.—Approximately 3.2 cm.

*Average width*.—Approximately 1.8 cm.

*Shape of blade*.—Spatulate to obovate.

*Apex*.—Obtuse.

*Base*.—Attenuate.

*Margin*.—Blunt dentate.

*Texture of top surface*.—Glabrous.

*Texture of bottom surface*.—Glabrous.

*Appearance of top surface*.—Matte.

*Appearance of bottom surface*.—Matte.

*Color*.—

*Young foliage upper side*.—Near Green 137A, fading lighter towards the base; 138B, margined yellow to yellow-green; in between 2B and 154B.

*Young foliage, under side*.—Near Green 137D, margined yellow-green; 154B and 154C, both colors present.

*Mature foliage, upper side*.—Near Green 137C, flushed greyed-green; 191B, margined white to green-white; in between 155A and 157A.

*Mature foliage, under side*.—Near Greyed-green 191B, margined white to yellow-white; in between 155A and 158C.

*Venation*.—Type: Pinnate. Venation color upper side: Near RHS Yellow-Green 144A. Venation color under side: Near RHS Green 143B.

*Petiole*.—Sessile.

FLOWER

Natural flowering season: Early summer to late Summer.

Inflorescence type: Axillary and terminal compound cyme.

Inflorescence size:

*Height*.—Approximately 6.5 cm.

*Width*.—Approximately 6.3 cm.

Quantity of inflorescence per plant: 150, depending upon maturity.

Quantity of flowers per inflorescence: Average 50.

Individual flowers: Rotate, single.

*Length*.—Approximately 5 mm.

*Diameter*.—Approximately 1.0 cm.

*Longevity on plant*.—About 14 days.

*Persistent or self-cleaning*.—Self-cleaning.

*Fragrance*.—Faint, typical moldy sweet.

Petals:

*Arrangement*.—Rotate.

*Quantity per flower*.—5.

*Size*.—Length: Approximately 10 mm. Width: Approximately 2 mm.

*Margin*.—Entire.

*Shape*.—Lanceolate.

*Apex*.—Acute.

*Base*.—Cuneate.

*Texture*.—Glabrous all surfaces.

*Appearance*.—Slightly glossy surfaces. Petal Color: When opening: Petal color, upper surface: Near RHS White N155D. Petal color, under surface: Near RHS White N155D. Petal Color, Fully opened: Upper surface: Near RHS White N155D slightly tinged Purple 75D. Under surface: Near RHS White N155D, slightly tinged Purple 75D. Color Changes when Aging: No significant change. Bud: Shape: Ovate. Length: Approximately 6 mm. Diameter: Approximately 2.5 mm. Color: Near RHS Green-White 157C. Texture: Glabrous. Appearance: slightly glossy. Calyx: Shape: Single whorl rotate, star-like. Length: 3.5 mm. Diameter: 1 mm. Sepals: Arrangement: Rotate. Quantity: 5. Shape: Narrow deltoid. Tip: Acute. Base: Cuneate. Margin: Entire. Texture: Glabrous all surfaces. Appearance: Slightly glossy all surfaces. Length of sepal: Approximately 5 mm. Width of sepal: Approximately 1.25 mm. Color upper surface: Near RHS Yellow-green 144A, margined lighter; 150D. Color lower surface: Near RHS Yellow-green 144A, margined lighter; 150D.

*Peduncle*.—Length: Average 5.3 cm. Width: Approximately 2 mm. Strength: Strong. Aspect: Straight, average able 30° from peduncle. Texture: Glabrous, moderately glossy. Color: Near RHS Yellow-green 146D, fading more yellowish towards proximal end, 152B.

*Pedicels*.—Length: Approximately 4 mm. Width: Approximately 1 mm. Aspect: Straight, average able 30° from peduncle. Strength: Moderately strong. Texture: Glabrous. Color: Near RHS Yellow-Green 146D.

REPRODUCTIVE ORGANS

Stamens: (Androecium).
*Number*.—Average 10.
*Filament length*.—Approximately 6 mm.
*Filament color*.—Near RHS Purple 76D.
*Anther length*.—0.15 mm.
*Anther color*.—Near RHS Greyed-Orange 173B.
*Anther shape*.—Basifixed, narrow oblanceolate.
*Pollen color*.—Near RHS Yellow 5C.
*Pollen quantity*.—Low.
Pistil: (Gynoecium).
*Number*.—Average 5.
*Length*.—Approximately 2 mm.
*Style color*.—Near RHS Purple 75D.
*Style length*.—Approximately 0.18 mm.
*Stigma*.—Shape: Linear. Color: Near RHS Purple 75B. Ovary Color: Near RHS White N155B.

OTHER CHARACTERISTICS

Fruits and seeds: Not observed to date.
Temperature tolerance: Tolerates temperatures from approximately −23° C. to at least 40° C.
Disease/pest resistance: Neither resistance nor susceptibility to normal diseases and pests of *Sedum* observed.
Drought tolerance: Drought resistance observed.

What is claimed is:

1. A new and distinct cultivar of *Sedum* plant named 'TAT1801' as herein illustrated and described.

* * * * *